United States Patent
Ozasa et al.

(10) Patent No.: US 6,750,060 B2
(45) Date of Patent: Jun. 15, 2004

(54) SHEATH LIQUID FOR PARTICLE ANALYZER

(75) Inventors: Masatsugu Ozasa, Kobe (JP); Junya Inoue, Kobe (JP); Masakazu Fukuda, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 10/395,272

(22) Filed: Mar. 25, 2003

(65) Prior Publication Data

US 2003/0180955 A1 Sep. 25, 2003

(30) Foreign Application Priority Data

Mar. 25, 2002 (JP) .......................... 2002-083457

(51) Int. Cl.[7] ............................... G01N 31/00
(52) U.S. Cl. .................. 436/10; 436/8; 436/18; 436/63; 436/164; 436/166; 435/2
(58) Field of Search ............... 436/8, 10, 18, 436/63, 164, 166; 422/73, 82.05, 82.09; 435/2

(56) References Cited

U.S. PATENT DOCUMENTS

| | | | |
|---|---|---|---|
| 3,661,460 A | | 5/1972 | Elking et al. .............. 356/36 |
| 4,523,841 A | * | 6/1985 | Brunsting et al. .......... 356/73 |
| 4,781,459 A | * | 11/1988 | Suzuki ...................... 356/335 |
| 5,757,475 A | * | 5/1998 | Katayama et al. ........... 356/73 |
| 5,891,733 A | * | 4/1999 | Inoue ........................ 436/63 |
| 6,025,201 A | | 2/2000 | Zelmanovic et al. |
| 2002/0020207 A1 | | 2/2002 | Shibta ...................... 73/1.36 |

FOREIGN PATENT DOCUMENTS

| | | |
|---|---|---|
| EP | 0214614 A2 | 3/1987 |
| EP | 0398522 A2 | 11/1990 |
| EP | 0582736 A1 | 2/1994 |
| EP | 0743356 A1 | 11/1996 |
| JP | 61-266959 A | 11/1986 |
| JP | 62-87233 A | 4/1987 |
| JP | 7-82010 B2 | 9/1995 |
| JP | 8-33388 B2 | 3/1996 |
| JP | 8-122327 A | 5/1996 |
| JP | 8-170960 A | 7/1996 |

OTHER PUBLICATIONS

Cucci et al. "Effects of Mismatched Refractive Indices in Aquatic Flow Cytometry". Cytometry, vol. 44, pp. 173–178, 2001.*

* cited by examiner

Primary Examiner—Maureen M. Wallenhorst
(74) Attorney, Agent, or Firm—Birch, Stewart, Kolasch & Birch, LLP

(57) ABSTRACT

A sheath liquid for use with a particle analyzer has a refractive index of 1.3340 or more at the wavelength of sodium D line at 25° C.

17 Claims, 3 Drawing Sheets

SHEATH LIQUID FOR PARTICLE ANALYZER

CROSS-REFERENCE TO RELATED APPLICATION

This application is related to Japanese Patent Application No. 2002-83457 filed on Mar. 25, 2002, whose priority is claimed under 35 USC §119, the disclosure of which is incorporated by reference in its entirety.

BACKGROUND OF THE INVENTION

1. Field of the Invention

The present invention relates to a sheath liquid for a particle analyzer.

2. Description of Related Art

In recent years, there have emerged apparatus using a sheath flow system for discriminating and/or analyzing cells or fine particles, and the discrimination and analysis of biological samples such as blood, urine and the like are more and more highly automated and are speeded faster and faster.

The sheath flow system is a technique for obtaining the count of and morphological information about cells or particles. The cells or particles, as they are or in the form of a suspension or a diluted sample, are enveloped in a stream of a sheath liquid and are passed one by one at an optimal flow amount and flow velocity in a flow cell of a flow cytometer. The count and morphological information are obtained by detecting an electrical or optical pulse generated by the cells or particles when passing by a detecting section in the flow cell.

For example, a sample containing object cells, particles and the like is lead by the steam of the sheath liquid to a detecting section, where the cell or particles are irradiated with a laser beam from a laser light source via a lens for focusing light emitted from the light source. The emitted light is stopped by an emitted light stopper, and only forward scattered light from the cells or particles is detected by a forward scattered light detector via a lens for detecting forward scattered light. On the other hand, side scattered light is detected by a side scattered light detector via a lens for detecting side scattered light. Voltage values detected by the detectors are input to an analyzer, which produces a scattergram by the forward and side scattered light based on the voltage values, displays the scattergram on a display and counts the cells and particles.

In the case where the laser light source is a red light source such as a He-Ne laser, a semiconductor laser or the like, no problems are observed with samples like blood which are diluted at a high dilution factor, but accurate analysis results cannot be obtained with samples like urine which are used as they are or which are diluted at a low dilution factor.

More particularly, in the case of a sample like urine intrinsically having a high refractive index, the sample and the sheath liquid have greatly different refractive index at a wavelength near red. Consequently a baseline of a forward scattered light signal fluctuates, and a population may appear in a scattergram as if a lot of particles existed although particles are not present in the sample. Therefore, particulate components in the sample cannot be counted accurately.

SUMMARY OF THE INVENTION

An object of the present invention is to provide a sheath liquid for a particle analyzer that allows a sample having a high refractive index to be analyzed accurately even with use of a red light source.

The present invention provides a sheath liquid for use with a particle analyzer having a refractive index of 1.3340 or more (preferably 1.3380 to 1.3450) at the wavelength of sodium D line at 25° C.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
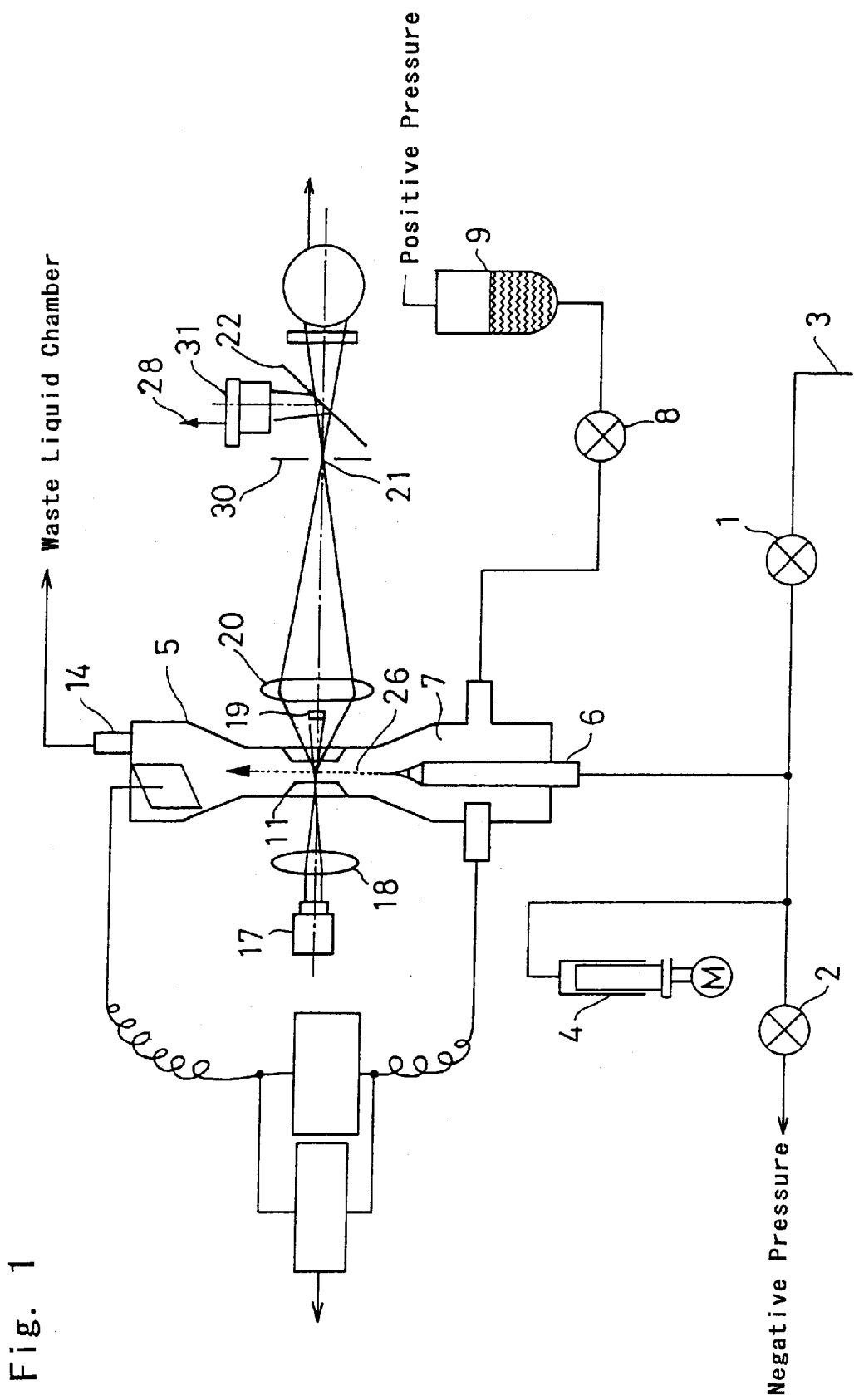
FIG. 1 is a schematic diagram of a particle analyzer for which the sheath liquid of the present invention can be suitably used.

The sheath liquid of the present invention is usually for enveloping a sample containing particles to be analyzed and passing them through a flow cell of a flow cytometer at an optimal flow amount and velocity for the purpose of analyzing the particles using the flow cytometer.

The composition of the sheath liquid is not particularly limited insofar as the cells or particles in the sample are not affected by the sheath liquid, and may be adjusted as appropriate depending upon the kind and concentration of the sample, the type of a light source used with the flow cytometer and the like. Sheath liquids usually contain buffer agents, osmotic pressure compensating agents, surfactants, chelating agents, fungicidal agents/bactericidal agents and the like in organic solvents, water or mixture thereof. The sheath liquid of the present invention may also be composed to contain at least one of, preferably a plurality of the above-mentioned components.

More particularly, the buffer agents are used for maintaining the pH of the sheath liquid within the range of about 6.0 to 8.5, preferably about 7.0 to 8.5. The buffer agents may be conventionally known ones, and examples thereof include Tris buffers, Good's buffers such as MES, Bis-Tris, ADA, PIPES, ACES, MOPSO, BES, MOPS, TES, HEPES, DIPSO, TAPSO, POPSO, HEPPSO, EPPS, Tricine, Bicine and TAPS, disodium hydrogen phosphate, sodium dihydrogen phosphate, potassium dihydrogen phosphate, veronal sodium-HCl, collidine-HCl, tris(hydroxymethyl) aminomethane-HCl and the like. The concentration may be adjusted as appropriate depending upon the buffer capacity of a buffer agent used and may be about 5 to 50 mM, for example.

The osmotic pressure compensating agents are used for preventing the cells or particles in the sample from lysing and maintain the osmotic pressure of the sheath liquid. Examples thereof include inorganic salts such as sodium chloride, potassium chloride, lithium chloride and the like, organic salts such as propionates (e.g., sodium propionate, potassium propionate, ammonium propionate, etc.), oxalates, acetates and the like, and saccharides such as sorbitol, glucose, mannitol and the like.

The surfactants are not necessarily contained in the sheath liquid, but may be cationic, anionic, nonionic or ampholytic insofar as they do not affect the analysis of the sample adversely. The surfactants may preferably be nonionic. Preferable examples thereof are as follows:

polyoxyethylenealkyl ether-type surfactants (see Japanese Unexamined Patent Publication No. HEI 8(1996)-122327) such as those of the formula:

wherein R is $C_{8-22}$ alkyl or alkylene group, n is an integer of 25 to 35, for example, $C_{12}H_{25}$—O—$(CH_2CH_2$—O$)_{30}$—H, $C_{18}H_{35}$—O—$(CH_2CH_2$—O$)_3O$—H, $C_8H_{17}$—O—$(CH_2CH_2$—O$)_{30}$—H and $C_{22}H_{45}$—O—$(CH_2CH_2$—O$)_{30}$—H;

polyoxyethylenealkylphenyl ether-type surfactants (see Japanese Patent Publication No. HEI 8(1996)-33388) having $C_{9-20}$ alkyl group and 20 to 60 of an additional mole number of polyoxyethylene, for example, Nissannonion NS-240;

polyoxyethylenesorbitanalkyl ester-type surfactants (see Japanese Patent Publication No. HEI 7(1995)-82010) having alkyl group with a carbon number 16 or more and 15 to 40 of an additional mole number of polyoxyethylene, for example, RHEODOL TW-0120 produced by Kao Corporation;

polyol copolymers having a hydroxyl group at the end (see Japanese Unexamined Patent Publication No. SHO 62(1987)-87233) such as those of the formula:

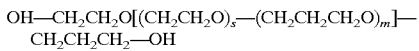

wherein s and m are, the same or different, 39 to 77, for example Pluronic P-105, P-84, P-85, P-87, P-75 and the like produced by BASF Wyandotte Company;

MEGA-8;

sucrose monocaprate;

deoxy-BIGCHAP;

n-octyl-β-D-thioglucoside, n-nonyl-β-D-thiomaltoside, n-heptyl-β-D-thioglucoside, n-octyl-β-D-thioglucoside;

CHAPS, CHAPSO and the like. The surfactants may be used in a concentration of about 50 to 5000 mg/L, preferably about 100 to 3000 mg/L.

The chelating agents are used for dissolving amorphous salts (e.g., ammonium phosphate.magnesium, calcium carbonate) present in the sample and for anti-oxidation. Examples thereof include EDTA salts, CyDTA, DHEG, DPTA-OH, EDDA, EDDP, GEDTA, HDTA, HIDA, Methy-EDTA, NTA, NTP, NTPO, EDDPO and the like. The concentration may be within the range of about 0.05 to 5 W/W %.

The fungicidal agents/bactericidal agents are not particularly limited, and usable examples thereof include triazine antimicrobial agents, thiazole antimicrobial agents such as benzisothiazolone (BIT), pyrithione (PTO), pyridine antimicrobial agents such as 1-hydroxypyridine-2-thiosodium, 2-phenoxyethanol and the like. These agents are required to be added to the sheath liquid in a concentration such that they do not affect the analysis of the sample adversely.

Suitably the organic solvents are aqueous organic solvents, and examples thereof include lower alkanols, lower alkylene glycols and lower alkylene glycol monolower alkyl ethers. Particularly, are usable methanol, ethanol, n-propanol, ethylene glycol, diethylene glycol, triethylene glycol, ethylene glycol mono-methyl ether and ethylene glycol mono-ethyl ether, among which ethylene glycol and diethylene glycol and triethylene glycol are preferable. Ethylene glycol is the most preferable in consideration of its influence on the cells or particles in the sample and its viscosity.

In the present invention, the refractive index of the sheath liquid can be adjusted by varying the kind and/or concentration of each component in the sheath liquid. For example, about 6.2 g/L of sodium chloride can be used for raising the refractive index of the sheath liquid by 0.001, while about 11 g/L of ethylene glycol can be used for raising the refractive index by 0.001. Thus, the above-mentioned agents and solvents may be used singly or as a combination of two or more thereof in an appropriate concentration so that components contained in the sample such as cells, particles and others will not be adversely affected.

The refractive index of the sheath liquid of the present invention at the wavelength of sodium D line ($\lambda$=589.3 nm) is set equal to the refractive index of the sample to be analyzed at 25° C. Here the term "equal" means that the sheath liquid has a refractive index within the range of the refractive index of the sample ±0.5%, preferably ±0.3%.

The sample to be analyzed is not particularly limited, but may suitably be a biological sample, more particularly, blood, urine, spinal fluid and the like. Suitably the sample has a refractive index of 1.3340 or more, preferably within the range of 1.3380 to 1.3450, more preferably about 1.3400 to 1.3420 at the wavelength of sodium D line at 25° C. The sheath liquid of the present invention, in particular, is useful for analysis of urine, and a urine sample preferably has a refractive index of 1.3380 to 1.3450.

In the present invention, the refractive index is based on that at the wavelength of sodium D line. Accordingly, in the case where the flow cytometer uses a light source with a wavelength of about 500 nm or more, or about 500 to 800 nm (a He—Ne laser, a red semiconductor laser, etc.), the sheath liquid may have a refractive index equal to that of the sample at the wavelength of a light source used. In addition, the refractive index of the sheath liquid may be equal to that of the sample not at 25° C. but at temperature at the time when the sheath liquid and the sample are passed through the flow cell, for example, at about 25 to 45° C. in consideration of a reaction which may take place in the sample and other factors.

According to the present invention, the particles contained in the sample may be analyzed using a flow cytometer as typically shown in FIG. 1. First a valve 1 and a valve 2 are opened for a specific time period to introduce the sample from a suction nozzle 3 into a path between the valves 1 and 2 by negative pressure from a waste liquid chamber. Subsequently, the valves 1 and 2 are closed and a syringe 4 pushes out a liquid, thereby delivering the sample from a sample nozzle 6, and at the same time a valve 8 is opened to supply the sheath liquid from a sheath liquid chamber 9 into a chamber 7 of a flow cell 5. Thereby the sample is made thin by the inner diameter of the chamber 7 to form a sheath flow together with the sheath liquid. Then the sheath flow passes through an orifice 11. The orifice 11 is formed of an optical glass (including quartz glass) in the shape of a prism which is about 100 to 300 μm wide on the inside. This formation of the sheath flow allows the particles to flow through the center of the orifice 11 one by one in a line. The particles having passed through the orifice 11 are discharged with the sheath liquid through a collecting tube 14 mounted on a chamber 7.

The sample 26 flowing almost at the center of the orifice 11 is irradiated with a laser beam which is emitted from a laser 17 and condensed to be ellipse in cross section by a condenser lens 18. More particularly, the laser beam is condensed so that its cross section has a dimension almost equal to the diameter of the cells or particles in the direction of the flow of the sample while it has a dimension considerably larger than the diameter of the cells or particles in a direction perpendicular to the flow of the sample and to the optical axis of the emitted laser beam. For example, the laser beam is around 10 μm in the sample flow direction and around 150 to 300 μm in the direction perpendicular to the flow of the sample and to the optical axis of the emitted laser beam. Of the laser beam applied to the flow of the sample, light which has not impinged on cells or particles (material objects) and has traveled through the flow cell 5 is stopped by a beam stopper 19, while light which has impinged on cells or particles (material objects) and has been scattered at small angles, i.e., forward scattered light, is collected by a collector lens 20 and passes through a pin hole 21 of a light shielding plate 30. Then the forward scattered light reaches a dichroic mirror 22, which reflects the forward scattered light. The forward scattered light is then received by a photo diode 31 and converted into an electric signal 28, which is output.

Output electric signals are input to the analyzer, which displays a scattergram by plotting the values of the signals corresponding to the forward scattered light for use in counting cells or particles.

The sheath liquid of the present invention is useful for measuring scattred light, in general, scattered light that is able to be measured by commercially available flow cytometers. The scattered light includes a low-angle forward scattered light (at an acceptance angle of 0 to less than 5 degrees, for example), a high-angle forward scattered light (at an acceptance angle of around 5 to 20 degrees, for example), a side scattered light (at an acceptance angle of around 90 degrees) and the like. The sheath liquid of the present invention is particularly useful for measuring the forward scattered lights.

The present invention also includes (1) a sheath liquid for use with a particle analyzer, for enveloping particles contained in a sample to be analyzed by a flow cytometer and passing the particles through a flow cell of the flow cytometer, the sheath liquid having a refractive index at the wavelength of sodium D line equal to that of the sample at 25° C., (2) a preparation method of preparing a sheath liquid for use with a particle analyzer, for enveloping particles contained in a sample to be analyzed by a flow cytometer and passing the particles through a flow cell of the flow cytometer, the method comprising setting the refractive index of the sheath liquid to be equal to the refractive index of the sample at wavelength of sodium D line at 25° C., and (3) a particle analysis method comprising, for analyzing particles contained in a sample to be analyzed by a flow cytometer, enveloping the particles with a sheath liquid having a refractive index at the wavelength of sodium D line equal to that of the sample at 25° C. and passing the particles through a flow cell of the flow cytometer.

The sheath liquid for a particle analyzer of the present invention is described in detail by way of example.

Sheath liquids having the following compositions were prepared for analyzing, respectively, as a sample to be analyzed by use of a flow cytometer, a urine sample from which particulate components had been removed by filtration with a 0.22 μm filter. The urine sample had a refractive index of 1.3419 at the wavelength of sodium D line at 25° C.

TABLE 1

Sheath Liquid 1

| Components | Amount | Effect |
| --- | --- | --- |
| Purified water | 1 kg (1.0 L) | |
| NaCl | 53.0 g | Refraction index adjustment |
| Maleic acid | 0.5 g | pH adjustment |
| Tris(hydroxymethyl) aminomethane | 1.51 g | pH adjustment |
| EDTA-2K | 0.2 g | Anti-oxidation |
| Polyoxyethylene (20) sorbitan mono-oleate (nonionic surfactant) | 1.5 g | Debubbling |
| 2-phenoxyethanol | 1.0 g | Fungicide |
| Refractive index | 1.3420 | |
| pH | 7.8 | |

Sheath Liquid 2

| Components | Amount |
| --- | --- |
| Purified water | 1 kg (1.0 L) |
| NaCl | 53.0 g |
| Maleic acid | 0.5 g |
| Tris(hydroxymethyl) aminomethane | 1.51 g |
| EDTA-2K | 0.2 g |
| Refractive index | 1.3420 |
| pH | 7.8 |

For comparison, the sheath liquid of Japanese Patent Publication of HEI 7(1995)-82010 was prepared. The measurement of properties of this sheath liquid showed an nD of 1.335, and a pH of 7.2.

The sheath liquid 1 and the sheath liquid for comparison were used for measuring the forward scattered light of the urine sample using a flow cytometer provided with a light source of 633 nm wavelength. The measurement results are shown in FIGS. 2(a) and 3(a).

Figure 2A:
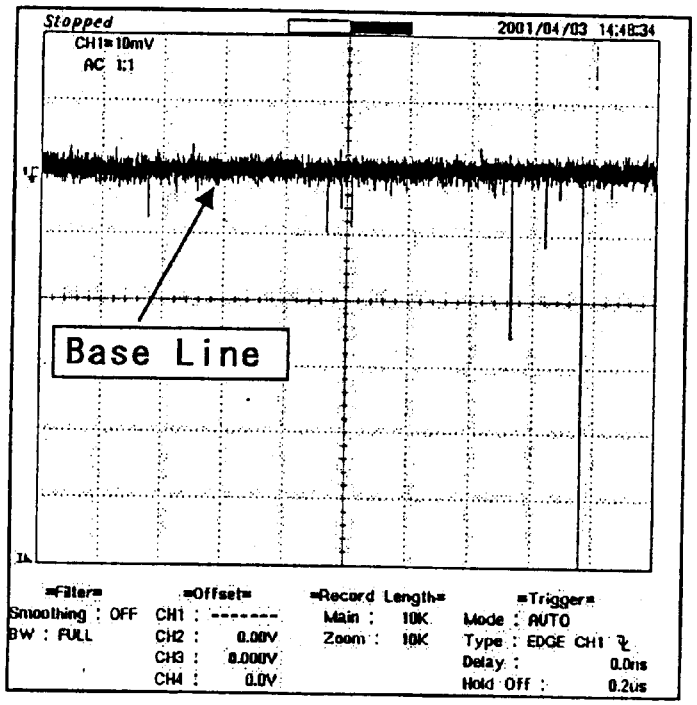
FIG. 2($a$) is a graph showing a baseline when a forward scattered light signal is measured with use of the sheath liquid 1 for a particle analyzer of the present invention, and FIG. 2($b$) is a scattergram by forward scattered light measured with use of the sheath liquid 1 of the present invention.
Figure 2B:
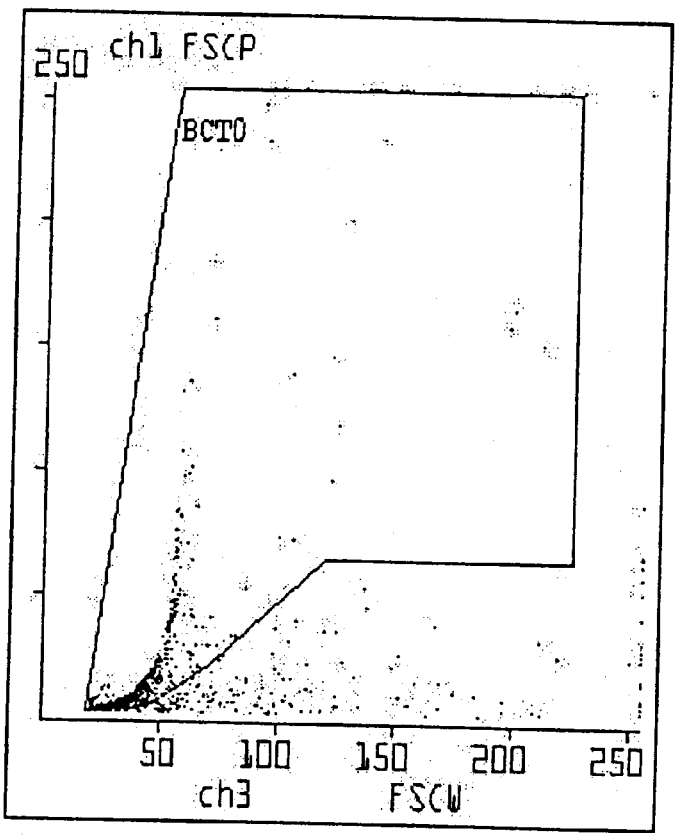

FIG. 2(a) shows that, according to the present invention, the baseline of the forward scattered light was suppressed from vacillating because the refractive index of the sheath liquid 1 was substantially equal to that of the urine sample. Consequently, as shown in the scattergram of FIG. 2(b), the counting of false components in the urine sample was restrained, and the urine sample was able to be analyzed accurately.

Figure 3A:
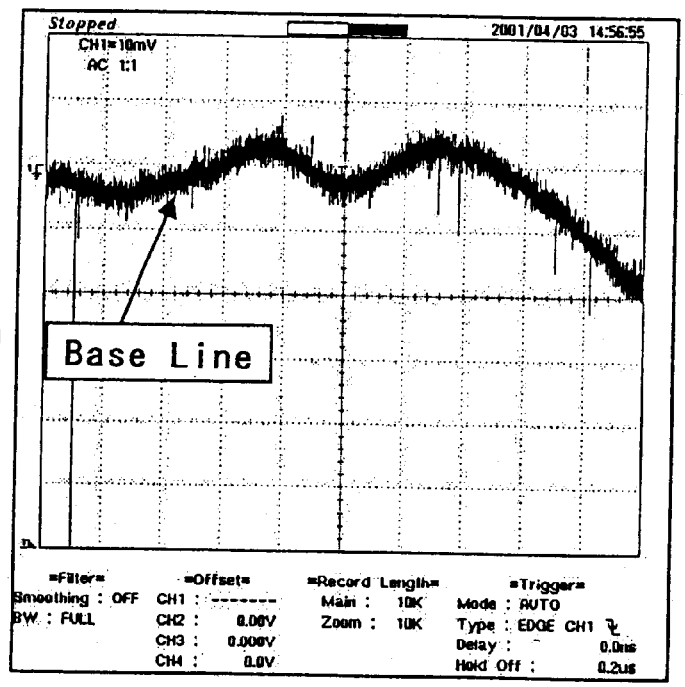
FIG. 3($a$) is a graph showing a baseline of a forward scattered light signal measured with use of a conventional sheath liquid for a particle analyzer, and FIG. 3($b$) is a scattergram by forward scattered light measured with use of the conventional sheath liquid.
Figure 3B:
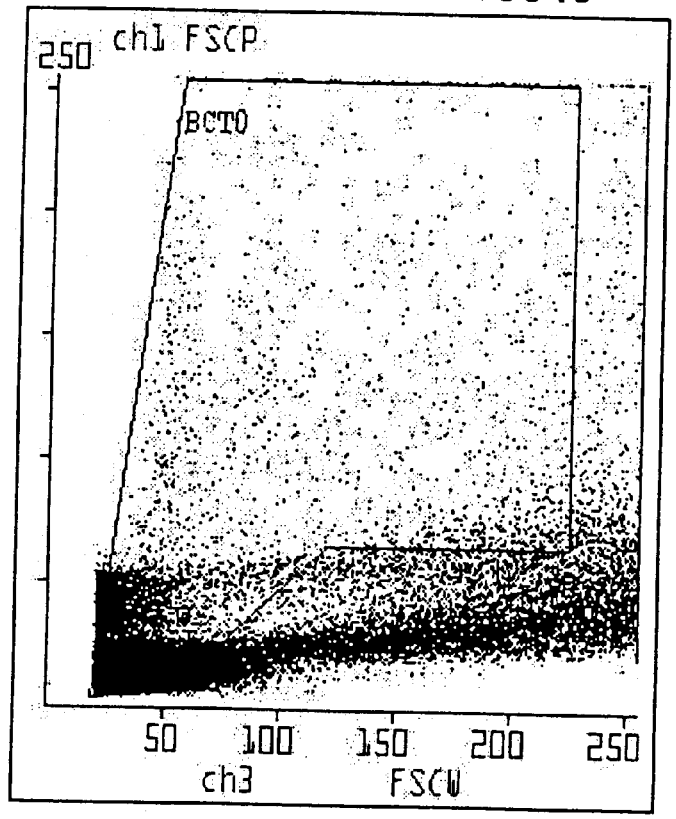

In contrast, by use of the conventional sheath liquid, a large vacillation was observed in the baseline of the forward scattered light, as shown in FIG. 3(a), owing to the difference between the refractive index of the sheath liquid and that of the urine sample. Consequently, as shown in the scattergram of FIG. 3(b), a large number of false components in the urine sample were counted.

What is claimed is:

1. A sheath liquid for use with a particle analyzer having a refractive index of 1.3340 or more at a wavelength of sodium D line at 25° C.

2. A sheath liquid according to claim 1, wherein the refractive index is within the range of 1.3380 to 1.3450 at the wavelength of sodium D line at 25° C.

3. A sheath liquid according to claim 1, comprising at least one component selected from the group consisting of a buffer agent, an osmotic pressure compensating agent, a surfactant, a chelating agent and a fungicidal agent/bactericidal agent, the component being contained in an organic solvent, water or mixture thereof.

4. A sheath liquid according to claim 3, wherein the buffer agent maintains the pH of the sheath liquid within the range of about 6.0 to 8.5.

5. A sheath liquid according to claim 4, wherein the buffer agent is selected from the group consisting of tris buffers, Good's buffers such as MES, Bis-Tris, ADA, PIPES, ACES, MOPSO, BES, MOPS, TES, HEPES, DIPSO, TAPSO, POPSO, HEPPSO, EPPS, Tricine, Bicine and TAPS, disodium hydrogenphosphate, sodium dihydrogen phosphate, potassium dihydrogen phosphate, veronal sodium-HCl, collidine-HCl and tris(hydroxymethyl) aminomethane-HCl.

6. A sheath liquid according to claim 3, wherein the surfactant is selected from the group consisting of polyoxyethylenealkyl ether-type surfactants, polyoxyethylenealkylphenyl ether-type surfactants, polyoxyethylenesorbitanalkyl ester-type surfactants, polyol copolymers having a hydroxyl group at the end, MEGA-8, sucrose monocaprate, deoxy-BIGCHAP, n-octyl-β-D-thioglucoside, n-nonyl-β-D-thiomaltoside, n-heptyl-β-D-thioglucoside, n-octyl-β-D-thioglucoside, CHAPS and CHAPSO.

7. A sheath liquid according to claim 6, wherein the surfactant is used in a concentration of about 50 to 5000 mg/L.

8. A sheath liquid according to claim 1, comprising 1 kg of purified water, 20 to 78 g of NaCl, 5 to 50 mM of maleic acid, 5 to 50 mM of tris(hydroxymethyl)aminomethane, 0.05 to 5 w/w % of EDTA-2K, 0.05 to 5 g of polyoxyethylene (20) sorbitan mono-oleate as a nonionic surfactant and 0.1 to 3.0 g of 2-phenoxyethanol.

9. A sheath liquid according to claim 1, comprising, 1 kg of purified water, 20 to 78 g of NaCl, 5 to 50 mM of maleic acid, 5 to 50 mM of tris(hydroxymethyl)aminomethane and 0.05 to 5 w/w % of EDTA-2K.

10. A sheath liquid for use with a flow cytometer, for enveloping a sample containing particles to be analyzed by the flow cytometer and passing the particles through a flow cell of the flow cytometer, the sheath liquid having a refractive index at a wavelength of sodium D line equal to that of the sample at 25° C.

11. A sheath liquid according to claim 10, wherein the sample has the refractive index of 1.3340 or more at the wavelength of sodium D line at 25° C.

12. A sheath liquid according to claim 10, wherein the sheath liquid has the refractive index within the range of the refractive index of the sample ±0.5%.

13. A sheath liquid according to claim 10, wherein the flow cytometer uses a light source with a wavelength of about 500 nm or more.

14. A particle analysis method for analyzing particles in a sample containing particles to be analyzed by a flow cytometer, comprising enveloping the sample with a sheath liquid having an refractive index at a wavelength of sodium D line equal to that of the sample at 25° C. and passing the sample enveloped by the sheath fluid through a flow cell of the flow cytometer.

15. A particle analysis method according to claim 14, wherein the sample has the refractive index of 1.3340 or more at the wavelength of sodium D line at 25° C.

16. A particle analysis method according to claim 15, wherein the analysis of the particles by the flow cytometer is based on forward scattered light.

17. A particle analysis method according to claim 14, wherein the sample has the refractive index of 1.3380 to 1.3450 at the wavelength of sodium D line at 25° C.

* * * * *